United States Patent [19]

Wason et al.

[11] 4,140,757
[45] Feb. 20, 1979

[54] EXTENSION OF GUM THICKENER WITH SILICON DIOXIDE AND TOOTHPASTE CONTAINING THE SAME

[75] Inventors: Satish K. Wason, Churchville; Robert K. Mays, Havre de Grace, both of Md.

[73] Assignee: J. M. Huber Corporation, Locust, N.J.

[21] Appl. No.: 813,323

[22] Filed: Jul. 6, 1977

Related U.S. Application Data

[63] Continuation-in-part of Ser. No. 597,621, Jul. 21, 1975, abandoned.

[51] Int. Cl.² .................................................. A61K 7/16
[52] U.S. Cl. ........................................ 424/49; 424/357
[58] Field of Search ................................ 424/49–58, 424/357; 423/339; 252/317

[56] References Cited

U.S. PATENT DOCUMENTS

| | | | |
|---|---|---|---|
| 2,523,204 | 9/1950 | Feustel et al. | 252/351 |
| 3,235,331 | 2/1966 | Nauroth et al. | 423/339 |
| 3,445,189 | 5/1969 | Maat et al. | 423/339 X |
| 3,538,230 | 11/1970 | Pader et al. | 424/52 X |
| 3,689,637 | 9/1972 | Pader | 424/52 |
| 3,705,940 | 12/1972 | Kirchgassner | 424/49 |
| 3,711,604 | 1/1973 | Colodney et al. | 424/52 |
| 3,716,493 | 2/1973 | Acker et al. | 252/317 |
| 3,803,301 | 4/1974 | Cordon et al. | 424/49 |
| 3,836,641 | 9/1974 | Hoyles et al. | 424/49 |
| 3,840,657 | 10/1974 | Norfleet | 424/49 |
| 3,842,167 | 10/1974 | Block et al. | 424/49 |
| 3,864,470 | 2/1975 | Watson | 424/49 |
| 3,893,840 | 7/1975 | Wason | 106/288 B |
| 3,906,090 | 9/1975 | Colodney | 424/52 |
| 3,911,102 | 10/1975 | Harrison | 424/49 |
| 3,911,104 | 10/1975 | Harrison | 424/52 |
| 3,928,541 | 12/1975 | Wason | 423/339 |
| 3,929,987 | 12/1975 | Colodney et al. | 424/52 |
| 3,934,000 | 1/1976 | Barth | 424/49 |
| 3,935,306 | 1/1976 | Roberts et al. | 424/49 |
| 3,939,262 | 2/1976 | Kim | 424/52 |

*Primary Examiner*—Shep K. Rose
*Attorney, Agent, or Firm*—Robert L. Price; Harold H. Flanders

[57] ABSTRACT

The extension of a gum thickener in a dentifrice composition of high water content is achieved by replacement of up to 50% of the gum thickener with a silica thickener which results in a dentifrice of improved cosmetic properties while reducing total raw material costs.

13 Claims, No Drawings

EXTENSION OF GUM THICKENER WITH SILICON DIOXIDE AND TOOTHPASTE CONTAINING THE SAME

CROSS-REFERENCE TO RELATED APPLICATIONS

The present application is a continuation-in-part of U.S. application Ser. No. 597,621, filed July 21, 1975, now abandoned and is related to U.S. application Ser. No. 402,927, filed Oct. 3, 1973, entitled "PROCESS FOR PRODUCING PRECIPITATED THICKENER SILICA" by Satish K. Wason and commonly assigned with the present application, now U.S. Pat. No. 3,967,563.

BACKGROUND OF THE INVENTION

1. Field of the Invention

In general, the present invention relates to dentifrice compositions and more specifically to the extension of gum thickeners by replacement of a portion thereof with a silica thickener.

2. Description of the Prior Art

Present day toothpastes are composed of five essential components; that is, an abrasive material, a thickener material, a humectant system, flavor, and foaming agent. An excellent review entitled "Dentifrices" is presented by S. D. Gershon and Morton Pader in *Cosmetics: Science and Technology*, Volume 1, Second Edition, pages 423–531.

On page 490, the use of binders in dentifrices is discussed and the pertinent information is included here as a reference.

"Simple admixture of the solid and liquid phases of a toothpaste is inadequate to prevent separation of the liquid phase, particularly during storage. To avoid this, a binder is added. Essentially all binders are hydrophilic colloids which appear to dissolve but actually disperse, swell, or absorb water to form viscous liquid phases. By acting as protective colloids and by increasing the consistency of the mixture of liquid and solid phases of the toothpaste, the binder stabilizes the mass against separation of the liquid phase.

Starch, which was generally employed in the form of glycerite of starch was one of the first binders employed. Gum arabic, ghatti, gums karaya and tragacanth, natural tree exudations, were prominent as binders during the early part of the twentieth century. Seaweed colloids, as represented by Irish moss and the alginates, have gained prominence. Water-dispersible derivatives of cellulose, prepared synthetically, have been utilized recently to an increasing extent.

In addition to the organic binders, bentonite, a native colloidal, hydrated aluminum silicate, and Veegum, a complex colloidal magnesium aluminum silicate, have been recommended as binders."

In all dentifrice formulations, natural or synthetic, gum thickeners are used to provide the desired viscosity to the paste.

Viscarin is a thickener which is used in many dentifrices. It is refined water-soluble carrageenan extracted from certain red marine plants, reduced to a free-flowing powder by alcohol precipitation.

A synthetic thickener, CMC (carboxy methyl cellulose) is widely used in dentifrices.

The general procedure for using gum thickeners is that the thickener is first dispersed in the desired humectant system to form a gel. Then the other toothpaste ingredients are added to this gel.

Gum thickeners present many problems when these materials are used in locations of very high humidity; for example, in South America, Africa, and many Far East countries. Under the influence of high humidity conditions due to an enzyme attack, the gum thickener loses its efficiency. Both the CMC and viscarin lose their effectiveness to a considerable extent under high humidity conditions.

Normally, prior art dentifrice compositions which contain high loadings of water will contain about 1 wt. % of gum thickener. However, where the water content is low, the amount of thickener may similarly be lowered since there is less need for a large amount of thickener in the composition. Toothpaste compositions having low water contents and gum amounts of 0.2 to 2%, together with high contents of humectants, are shown in U.S. Pat. Nos. 3,934,000; 3,864,470; 3,935,306 and 3,689,637 for example. On the other hand, in dentifrice compositions which contain high water contents, e.g. in the range of 40 wt. %, about 1 wt. % of gum thickener is normally used as illustrated for example by U.S. Pat. No. 3,705,940.

The present invention provides a composition and method wherein dentifrice compositions having high water loadings can be formed with reduced amounts of gum thickeners.

SUMMARY OF THE INVENTION

We have discovered that stable dentifrices can be obtained by extending the functional performance of expensive gum thickeners with relatively inexpensive synthetic amorphous silicon dioxide. We have also discovered that viscosity of the finished toothpaste is influenced depending on the point of addition of silicon dioxide thickener to the paste. If the silicon dioxide is immediately added after the gel stage, no real advantages can be realized from such a silica thickener. But if the silicon dioxide is added along with the abrasive towards the end of the mixing procedure of the toothpaste formulation, real advantages of silica thickener can be fully realized. Silicon dioxide containing dentifrice is cheaper to manufacture than the corresponding ones containing only gum as a source of viscosity building properties. We have discovered that up to 50% of the gum thickener can be replaced by silicon dioxide thickener of the instant invention in compositions containing high amounts of water.

Accordingly, it is an object of the present invention to provide a new, highly effective method of extending or replacing a significant portion of the gum thickener in a dentifrice composition which overcomes the deficiencies of the prior art as described above.

It is also an object of the present invention to provide a new, highly effective dentifrice composition which overcomes the deficiencies of the prior art as described above.

It is further object of the present invention to provide a savings in raw material costs in dentifrice compositions.

Another object of the present invention is to improve the ease of handling solid particulate silicon dioxide thickeners in conjunction with gum thickeners under high levels of humidity.

A further object of the present invention is to improve the cosmetic properties, luster and brightening properties of dentifrice compositions.

An additonal object of the present invention is to reduce slightly but still provide an effective level of overall abrasion characteristics in a dentifrice composition.

A further object of the present invention is to improve the deaeration characteristics of dentifrice compositions.

Other objects and a fuller understanding of the present invention may be had by referring to the following description taken in conjunction with the aforegoing background and the apended claims.

It is to be understood that the above statements of the "objects" of the present invention are statements representative of some of the advantages to be obtained by, and some of the reasons for, employing the present invention and are not intended to be construed as necessarily representing or reflecting the state of mind of the inventor prior to or at any stage during the process of conception and reduction to practice of the present invention.

The present invention may thus be seen to overcome the deficiencies of the prior art and to achieve its objectives by extending the functional performance of gum thickeners by a partial substitution of synthetic amorphous silicon dioxide for such gum thickeners at the time of addition of the dentifrice abrasive toward the end of the mixing procedure for such dentifrices.

According to the present invention there is provided a dentifrice composition comprising the following essential components:

| COMPONENT | AMOUNT - WT. % |
|---|---|
| Abrasive | 10 – 60 |
| Humectant | 15 – 40 |
| Gum Thickener | 0.4 – 0.9 |
| Silica Thickener | 1 – 20 |
| Water | 35 – 50 |
| Others | 0.1 – 5 |

In the above composition the materials identified as "Others" include flavoring agents, foaming agents, detergents or surfactants, coloring or whitening agents, preservatives, silicones, antibacterial agents, fluorides, and other materials normally found in dentifrice and toothpaste compositions.

The humectant system preferably comprises glycerine (glycerol) but may include other humectants such as sorbitol, all of which are well known in the art. The abrasive comprises any of the abrasives known to the dentifrice and toothpaste art including silica abrasives, calcium phosphates, silica xerogels, and the like, all of which are well known in the art.

The essence of the present invention resides in the concept that in dentifrice compositions having water loadings in the range of 35–50 wt. %, the amounts of expensive gum thickeners normally used to provide a cohesive composition, can be significantly reduced. Thus, it has been found that up to 50 wt. %, and preferably 20 to 50 wt. % of the gum thickeners can be replaced by certain high structure silicon dioxides. It has accordingly been found according to the present invention that suitable thickening of dentifrice compositions which contain high water amounts, for example, in the range of 35–50 wt. %, can be obtained by thickening with only about 0.4 to 0.9 wt. %, preferably 0.5 to 0.8 wt. %, of gum thickener in combination with about 1-20 wt. % of the high structure silica thickeners described herein.

DESCRIPTION OF THE PREFERRED EMBODIMENTS

In order to facilitate the understanding of the present invention, reference will now be made to certain preferred embodiments of the present invention which should not be construed as limiting the invention but are exemplary only.

The beneficial properties of silicon dioxide thickeners will become clear from the following examples.

EXAMPLE 1

The following dentifrices were prepared:

| | Parts | | | | |
|---|---|---|---|---|---|
| | A | B | C | D | E |
| Glycerine | 25.00 | 25.00 | 25.00 | 25.00 | 25.00 |
| Sodium Benzoate | 0.50 | 0.50 | 0.50 | 0.50 | 0.50 |
| Sodium Saccharin | 0.20 | 0.20 | 0.20 | 0.20 | 0.20 |
| CMC - 7MF | 1.00 | 0.50 | 0.50 | 0.50 | 0.50 |
| Sodium Monofluorophosphate | 0.76 | 0.76 | 0.76 | 0.76 | 0.76 |
| Water | 39.54 | 39.54 | 39.54 | 41.04 | 44.54 |
| Low Structure Silica Abrasive | 30.00 | 20.00 | 25.00 | 25.00 | 18.00 |
| High Structure Silica Thickener | 0.00 | 10.50 | 5.50 | 3.50 | 7.00 |
| Alumina | 1.00 | 1.00 | 1.00 | 1.00 | 1.00 |
| TiO$_2$ | 0.50 | 0.50 | 0.50 | 0.50 | 0.50 |
| Sodium Lauryl Sulfate | 1.50 | 1.50 | 1.50 | 1.50 | 1.50 |

Dentifrice composition A contained 30% silica abrasive and 1% CMC thickener. Composition B contained a total of 30.5% silica abrasive/thickener system and only 0.5% CMC. Composition C contained 30.5% of combined silica abrasive/thickener and only 0.5% CMC. Composition D contained 28.5% silica abrasive/thickener system and 0.5% CMC. Composition E contained only 25% silica abrasive/thickener system and only 0.5% CMC. The raw material cost of total abrasive/thickener of control (A) was compared with experimental compositions B through E. Compositions B through E represent 15 to 30% savings in total abrasive/thickener raw material cost with respect to control Composition A.

The stability characteristics of compositions B through E were compared with the control composition A. Compositions B and C were superior and compositions D and E were equal to the control in viscosity, texture and other cosmetic properties.

EXAMPLE 2

| | Parts | | |
|---|---|---|---|
| | F | G | H |
| Glycerine | 22.00 | 22.00 | 22.00 |
| Viscarin | 0.95 | 0.65 | 0.50 |
| Sodium Benzoate | 0.50 | 0.50 | 0.50 |
| Sodium Saccharin | 0.20 | 0.20 | 0.20 |
| TSPP | 0.25 | 0.25 | 0.25 |
| Detergent | 2.00 | 2.00 | 2.00 |
| Water | 21.10 | 21.10 | 21.10 |
| Dicalcium Phosphate Dihydrate | 52.00 | 50.30 | 49.45 |
| Flavor | 1.00 | 1.00 | 1.00 |
| Silica Thickener | 0.00 | 2.00 | 3.00 |

Composition F is a control containing only viscarin thickener. Composition G contained combined phosphate abrasive and silica thickener of 52.30% and only 0.65% viscarin. Composition H contained a combined phosphate abrasive and silica thickener at a level of 52.45% and only 0.5% viscarin. Note that experimental compositins G and H contain 31% and 47% lower amount of viscarin than the control composition F. Note also that the silica thickener in compositions G and H was pre-mixed with the phosphate polishing agent prior to adding it to the dentifrice formulation.

The stability characteristic of compositions G and H are equal to the control. Note compositions G and H represent about 15 to 30% savings in the raw material cost of thickener.

EXAMPLE 3

|  | Parts | | |
|---|---|---|---|
|  | I | J | K |
| Glycerine | 22.00 | 22.00 | 22.00 |
| Viscarin | 0.95 | 0.65 | 0.50 |
| Silica Thickener | 0.00 | 2.00 | 3.00 |
| Sodium Benzoate | 0.50 | 0.50 | 0.50 |
| Sodium Saccharin | 0.20 | 0.20 | 0.20 |
| TSPP | 0.25 | 0.25 | 0.25 |
| Detergent | 2.00 | 2.00 | 2.00 |
| Water | 21.10 | 21.10 | 21.10 |
| Dicalcium Phosphate Dihydrate | 52.00 | 50.30 | 49.45 |
| Flavor | 1.00 | 1.00 | 1.00 |

Compositions J and K are similar to compositions G and H except that the silica thickener was mixed with viscarin and then added to the humectant. Composition I is similar to composition F and was used as a control.

The stability data was collected on samples stored at 49° C. for nine weeks. Compositions J and K were not found equal to I in cosmetic and stability properties.

This result indicates that the silica thickener cannot be pre-mixed with the gum thickener to provide the needed viscosity. Example 2 taken in conjunction with the present example suggests the best point of addition of silica thickener is when the abrasive is pre-mixed with the silica thickener.

The dentifrice grade, low structure, precipitated silica abrasives employed in Example 1, compositions A, B, C, D and E were produced by methods as disclosed in U.S. Ser. No. 285,966, filed Sept. 5, 1972, now U.S. Pat. No. 3,928,541 and U.S. Ser. No. 402,928, filed Oct 3, 1973, now U.S. Pat. No. 3,960,586, by Satish K. Wason and assigned to the common assignee of the present application.

The high structure silica thickener of the present invention as employed in Example 1, compositions A, B, C, D and E; Example 2, compositions G and F; and Example 3, compositions J and K may be preferably produced in accordance with U.S. Ser. No. 402,927, filed Oct. 3, 1973 by Satish K. Wason, now U.S. Pat. No. 3,967,563, commonly assigned with the present invention and incorporated herein by reference. Regardless of the method of manufacture, the silica thickener of the present invention should have a primary particle size of less than 40 millimicrons; a void volume of from 3.0 to 6.0 cc Hg/g; an oil absorption of 150 to 250 cc oil/100 g of silica and preferably an oil absorption in excess of 200 cc oil/100 g of silica; and a surface area of from 100 to 400 m$^2$/g and preferably a surface area in excess of 250 m$^2$/g; and a wet cake moisture in excess of 85%.

The above silica products are sold by J. M. Huber Corporation under the trademarks Zeo ®, Zeodent ®, Zeosyl ®, Zeofree ®, and Zeothix ®.

In summary, the present invention extends the functional performance of gum thickeners by a partial substitution of synthetic amorphous silicon dioxide for a portion of the gum thickener at the time of addition of the abrasive to the dentifrice composition toward the end of the mixing procedure for such dentifrices.

Such use of a silica thickener exhibits the following advantages:

(1) Savings in raw material cost.

(2) Ease of handling the resulting thickener and maintaining the effectiveness thereof under any humidity level conditions.

(3) The use of silica thickener improves the cosmetic properties, luster and brightening properties of paste.

(4) The overall abrasion characteristics of the composition are slightly lowered by using the silica thickener.

(5) The silica thickener improves the deaeration characteristics of the toothpaste.

Although specific preferred embodiments of the present invention have been disclosed in the detailed description above, this description is not intended to limit the invention to the particular embodiments disclosed herein, since it will be obvious to those skilled in the art that they are illustrative rather than restrictive and that the invention is not so limited. The present invention is declared to cover all changes, modifications, substitutions, and equivalents of the specific examples and embodiments of the invention herein disclosed for purposes of illustration, which do not constitute departures from the essential teachings of and the spirit and scope of the invention as defined by the appended claims.

What is claimed is:

1. A dentifrice composition comprising the following essential components:

| COMPONENT | AMOUNT - WT. % |
|---|---|
| Abrasive | 10–60 |
| Humectant | 15–40 |
| Gum Thickener | 0.4–0.9 |
| Silica Thickener | 1–20 |
| Water | 35–50 | wherein said silica thickener has a primary particle size of less than 40 millimicrons, a void volume of from 3.0 to 6.0 cc Hg/g, an oil absorption of 150–250 cc oil/100 g of silica, a surface area of from 100–400 m$^2$/g, and a wet cake moisture in excess of 85%; and wherein said abrasive and said silica thickener are premixed prior to addition thereof to the other components of said dentifrice composition, said addition being at the conclusion of the mixing procedure for said other components.

2. A composition according to claim 1 wherein said abrasive is a low structure silica abrasive.

3. A composition according to claim 1 wherein said abrasive is dicalcium phosphate.

4. A composition according to claim 1 wherein said humectant is selected from the group consisting of glycerine, sorbitol and mixtures thereof.

5. A composition according to claim 1 wherein said gum thickener is carboxymethy cellulose.

6. A composition according to claim 1 wherein said silica thickener has an oil absorption value from 200 to 250 cc oil/100 g of silica and a surface area from 250 to 400 m$^2$/g.

7. A method of using a silica thickener to extend the functional performance of a gum thickener in a dentifrice composition comprising about 10–60 weight percent of an abrasive, about 15–40 weight percent of a humectant, about 0.4 to 0.9 weight percent of a gum thickener, and about 35–50 weight percent of water, said method comprising
 (a) premixing about 1–20 weight percent of a high structure silica thickener with said abrasive, and
 (b) adding the resulting mixture to the remaining components of said dentifrice composition at the conclusion of the mixing procedure for said remaining components;
 wherein said thickener has a primary particle size of less than 40 millimicrons; a void volume of from 3.0 to 6.0 cc Hg/g; an oil absorption of 150 to 250 cc oil/100 g of silica; a surface area of from 100 to 400 m$^2$/g; and a wet cake moisture in excess of 85%.

8. A method according to claim 7 wherein said abrasive is a low structure silica abrasive.

9. A method according to claim 7 wherein said abrasive is decalcium phosphate.

10. A method according to claim 7 wherein said humectant is selected from the group consisting of glycerine, sorbitol and mixtures thereof.

11. A method according to claim 7 wherein said gum thickener is carboxymethyl cellulose.

12. A method according to claim 7 wherein said silica thickener has an oil absorption value from 200 to 250 cc/100 g of silica and a surface area from 250 to 400 m$^2$/g.

13. a method according to claim 7 wherein the amount of gum thickener is about 0.5 to 0.8 weight percent.

* * * * *

UNITED STATES PATENT AND TRADEMARK OFFICE
CERTIFICATE OF CORRECTION

PATENT NO. : 4,140,757
DATED : February 20, 1979
INVENTOR(S) : Satish K. Wason and Robert K. Mays It is certified that error appears in the above-identified patent and that said Letters Patent are hereby corrected as shown below:

Column 3, line 16, "apended" should be -- appended --.

Column 5, line 3, "compositins" should be -- compositions --.

Column 5, line 8, "characteristic" should be -- characteristics --.

Column 6, Claim 5, "carboxymethy" should be -- carboxymethyl --.

Signed and Sealed this

Twelfth Day of June 1979

[SEAL]

Attest:

RUTH C. MASON
Attesting Officer

DONALD W. BANNER
Commissioner of Patents and Trademarks